US011903808B2

(12) United States Patent
Clarke et al.

(10) Patent No.: US 11,903,808 B2
(45) Date of Patent: Feb. 20, 2024

(54) ASSEMBLIES FOR STERILIZING A WET STORED PROSTHETIC HEART VALVE

(71) Applicant: Medtronic Vascular, Inc., Santa Rosa, CA (US)

(72) Inventors: David Clarke, Galway (IE); Karina Doyle, Galway (IE); Paul Devereux, Galway (IE); Gerry Kearns, Galway (IE); Padraigh Jennings, Galway (IE); Constantino Fiuza, Galway (IE); Stephen Montgomery, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 168 days.

(21) Appl. No.: 17/354,596

(22) Filed: Jun. 22, 2021

(65) Prior Publication Data

US 2021/0315679 A1  Oct. 14, 2021

Related U.S. Application Data

(62) Division of application No. 15/968,867, filed on May 2, 2018, now Pat. No. 11,284,984.

(Continued)

(51) Int. Cl.
*A61F 2/00* (2006.01)
*A61L 2/00* (2006.01)
(Continued)

(52) U.S. Cl.
CPC .............. *A61F 2/0095* (2013.01); *A61F 2/00* (2013.01); *A61F 2/2418* (2013.01);
(Continued)

(58) Field of Classification Search
CPC ........ A61F 2/0095; A61F 2/00; A61F 2/2418; A61F 2/2427; A61L 2/0088;
(Continued)

(56) References Cited

U.S. PATENT DOCUMENTS 3,167,075 A   1/1965  Paley et al.
3,326,450 A   6/1967  Langdon
(Continued)

FOREIGN PATENT DOCUMENTS

CN   105232187   1/2016
WO   98/36992    8/1998

OTHER PUBLICATIONS

International Search Report and Written Opinion for related International Application No. PCT/US2018/030587 dated Aug. 13, 2018 (13 pgs.).

(Continued)

*Primary Examiner* — Anna K Kinsaul
*Assistant Examiner* — Himchan Song
(74) *Attorney, Agent, or Firm* — Wentsler LLC

(57) ABSTRACT

Aspects of the disclosure relate to "wet" transcatheter prosthetic heart valve or other implant packaging and assemblies in which a prosthetic heart valve or other implant is loaded into a first portion of a delivery device and positioned within a container in which sterilizing fluid is retained to sterilize interior portions of the container as well as provide moisture to prevent the implant from drying out. The disclosure also relates to methods of sterilizing the disclosed assemblies. Some disclosed methods include at least two sterilizing steps and adjustment of a mechanical seal member or formation of multiple seals so that areas proximate the seals are also sterilized during the sterilization process.

10 Claims, 16 Drawing Sheets

Related U.S. Application Data

(60) Provisional application No. 62/595,618, filed on Dec. 7, 2017, provisional application No. 62/500,046, filed on May 2, 2017.

(51) Int. Cl.
    *A61F 2/24*           (2006.01)
    *B65D 81/22*        (2006.01)
    *B65D 81/18*        (2006.01)

(52) U.S. Cl.
CPC .......... *A61F 2/2427* (2013.01); *A61L 2/0088* (2013.01); *A61L 2/0094* (2013.01); *B65D 81/18* (2013.01); *B65D 81/22* (2013.01); *A61L 2202/181* (2013.01); *A61L 2202/21* (2013.01)

(58) Field of Classification Search
CPC ............. A61L 2/0094; A61L 2202/181; A61L 2202/21; B65D 81/18; B65D 81/22
USPC .......................................................... 53/425
See application file for complete search history.

(56) References Cited

U.S. PATENT DOCUMENTS

| | | | |
|---|---|---|---|
| 3,342,326 | A | 9/1967 | Zackheim |
| 4,176,746 | A | 12/1979 | Kooi |
| 4,211,325 | A | 7/1980 | Wright |
| 5,407,685 | A | 4/1995 | Malchesky et al. |
| 5,480,424 | A | 1/1996 | Cox |
| 5,720,391 | A | 2/1998 | Dohm et al. |
| 6,594,971 | B1 | 7/2003 | Addy et al. |
| 6,921,179 | B2 | 7/2005 | Diak Ghanem |
| 7,040,485 | B2 | 5/2006 | Gupta et al. |
| 7,631,760 | B2 | 12/2009 | Guelzow et al. |
| 7,712,606 | B2 * | 5/2010 | Salahieh ............... A61F 2/2427 206/370 |
| 7,748,525 | B2 | 7/2010 | Boyd |
| 7,866,468 | B2 | 1/2011 | Kyritsis |
| 8,297,439 | B2 | 10/2012 | Clark et al. |
| 8,851,286 | B2 | 10/2014 | Chang et al. |
| 8,973,748 | B2 | 3/2015 | Wu |
| 9,295,539 | B2 | 3/2016 | Hodshon et al. |
| 9,295,549 | B2 | 3/2016 | Braido et al. |
| 9,707,077 | B2 | 7/2017 | Chang et al. |
| 10,888,408 | B2 | 1/2021 | Ryan et al. |
| 2002/0120328 | A1 | 8/2002 | Pathak et al. |
| 2003/0029739 | A1 | 2/2003 | Riemenschneider et al. |
| 2005/0060022 | A1 | 3/2005 | Felt et al. |
| 2006/0108239 | A1 | 5/2006 | Iwatschenko |
| 2006/0113207 | A1 | 6/2006 | Ryan et al. |
| 2007/0050014 | A1 | 3/2007 | Johnson |
| 2007/0056149 | A1 | 3/2007 | Axel |
| 2007/0061008 | A1 | 3/2007 | Salahieh et al. |
| 2007/0065968 | A1 | 3/2007 | Kok et al. |
| 2007/0092398 | A1 | 4/2007 | McDonald |
| 2008/0102439 | A1 | 5/2008 | Tian et al. |
| 2008/0128296 | A1 | 6/2008 | Stopek et al. |
| 2009/0054976 | A1 | 2/2009 | Tuval et al. |
| 2009/0209031 | A1 | 8/2009 | Stopek |
| 2009/0234459 | A1 | 9/2009 | Sporring et al. |
| 2009/0287290 | A1 | 11/2009 | Macaulay et al. |
| 2010/0252470 | A1 * | 10/2010 | Ryan ..................... A61F 2/9525 206/370 |
| 2011/0004255 | A1 | 1/2011 | Weiner et al. |
| 2011/0113728 | A1 | 5/2011 | Falotico et al. |
| 2011/0147251 | A1 * | 6/2011 | Hodshon ............... A61F 2/2412 206/438 |
| 2011/0198244 | A1 * | 8/2011 | Murad .................. A61F 2/0095 206/210 |
| 2012/0158128 | A1 * | 6/2012 | Gautam .............. A61M 25/002 623/2.11 |
| 2012/0285123 | A1 | 11/2012 | Wang et al. |
| 2012/0301057 | A1 | 11/2012 | Conant et al. |
| 2013/0150957 | A1 | 6/2013 | Weber |
| 2013/0233736 | A1 | 9/2013 | Hess et al. |
| 2013/0248386 | A1 | 9/2013 | Benoit et al. |
| 2013/0272630 | A1 | 10/2013 | Thomas et al. |
| 2014/0067063 | A1 | 3/2014 | Bonutti |
| 2014/0110279 | A1 * | 4/2014 | Kruetzfeldt ............ B65D 77/24 359/726 |
| 2014/0158557 | A1 | 6/2014 | Dolan et al. |
| 2014/0202908 | A1 | 7/2014 | Liburd et al. |
| 2014/0270581 | A1 | 9/2014 | Jons |
| 2015/0122687 | A1 * | 5/2015 | Zeng ..................... A61F 2/0095 53/467 |
| 2015/0314942 | A1 | 11/2015 | Gwen |
| 2016/0030165 | A1 | 2/2016 | Mitra et al. |
| 2016/0128819 | A1 * | 5/2016 | Giordano .............. A61F 2/2427 623/2.11 |
| 2016/0207897 | A1 | 7/2016 | Wood et al. |
| 2016/0270897 | A1 | 9/2016 | Whiting et al. |
| 2016/0347492 | A1 | 12/2016 | Lu et al. |
| 2017/0049567 | A1 * | 2/2017 | Metchik ................ A61F 2/2433 |
| 2017/0056149 | A1 | 3/2017 | Rajpara et al. |
| 2017/0281329 | A1 * | 10/2017 | Chang ................... A61L 2/0088 |
| 2017/0325928 | A1 * | 11/2017 | Ino ........................ A61F 2/2436 |
| 2018/0140411 | A1 * | 5/2018 | Panus ................... A61F 2/2412 |
| 2018/0318060 | A1 * | 11/2018 | Ryan ........................ A61L 2/26 |
| 2018/0318061 | A1 | 11/2018 | Clarke et al. |
| 2019/0336262 | A1 * | 11/2019 | Duffy ....................... A61L 2/16 |
| 2020/0023100 | A1 | 1/2020 | Zucker et al. |

OTHER PUBLICATIONS

PCT Transmittal of the International Search Report and the Written Opinion from Application No. PCT/US2018/030575 dated Aug. 31, 2018 (11 pgs.).

Zhu et al., "The Effect of Glycerol on the Properties of the Cross-Linked Polyvinyl Alcohol Hydrogel Beads," Chemistry Europe, pp. 1 (Jan. 8, 2018) <https://chemistry-europe.onlinelibrary.wiley.com/doi.abs/10.1002/slct.201701975>.

* cited by examiner

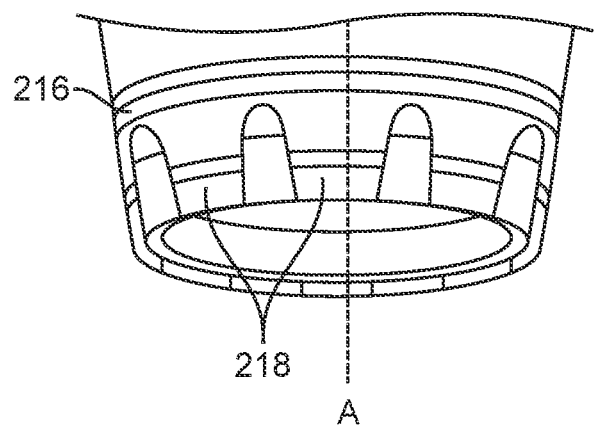
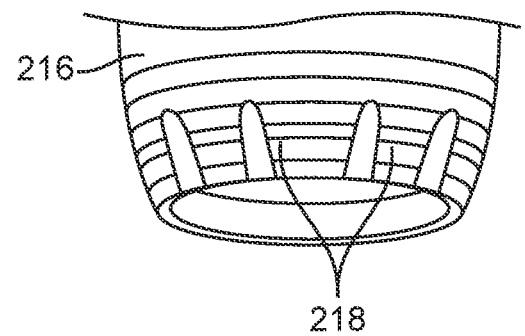
FIG. 8A  FIG. 8B
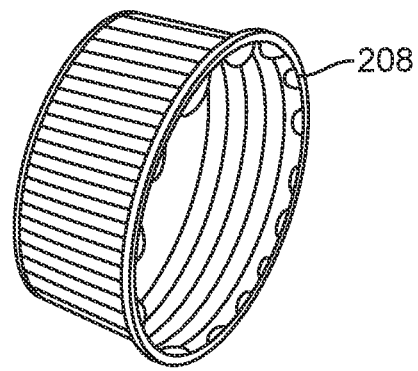
FIG. 9
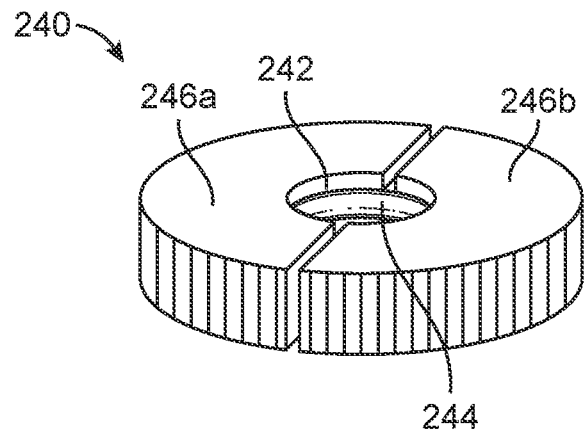
FIG. 10

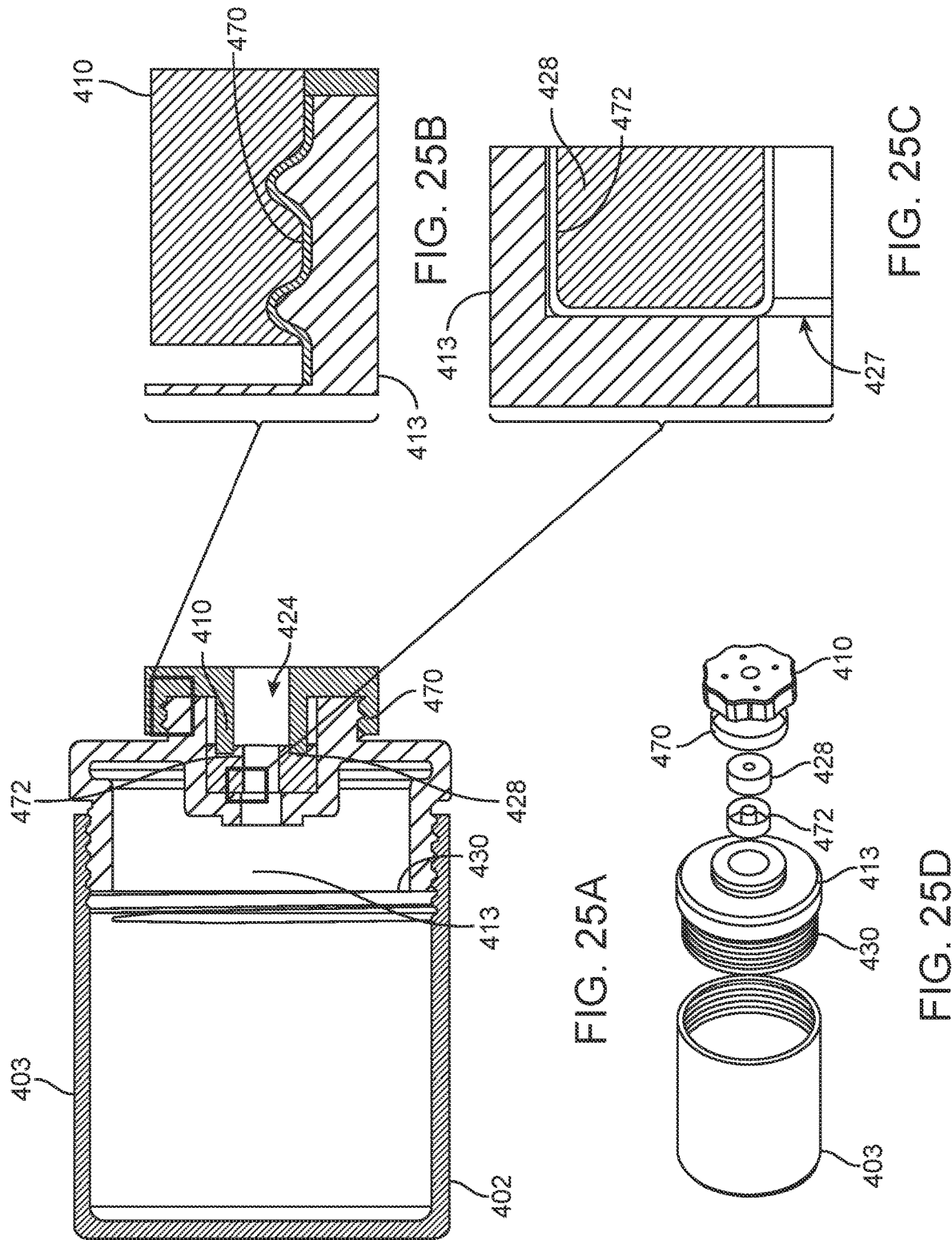

ASSEMBLIES FOR STERILIZING A WET STORED PROSTHETIC HEART VALVE

CROSS-REFERENCE TO RELATED APPLICATIONS

This application is a Divisional application of Ser. No. 15/968,867, filed May 2, 2018, entitled "ASSEMBLIES AND METHODS OF STERILIZING A WET STORED PROSTHETIC HEART VALVE" now allowed, which claims the benefit of the filing date of U.S. Provisional Patent Application Ser. No. 62/595,618, filed Dec. 7, 2017 and U.S. Provisional Patent Application Ser. No. 62/500,046, filed May 2, 2017, the entire teachings of which are incorporated herein by reference.

BACKGROUND

Disclosed embodiments relate to packaging for a "wet" tissue prosthetic heart valve or other implant with at least a portion of a delivery device. Methods of assembling packaged transcatheter prosthetic heart valves or implants with the portion of the delivery device and sterilizing the same are also disclosed.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter of a delivery device, inserted inside a body lumen of the patient, such as the femoral artery, and delivered to a desired location in the heart where the valve prosthesis is then deployed.

Known valve prostheses include a stent frame supporting a valve structure. The valve structure can assume a variety of forms, and can be formed, for example, from tissue made from one or more biocompatible synthetic materials, synthetic polymers, autograft tissue, homograft tissue, xenograft tissue, or one or more other suitable materials. In some embodiments, the valve structure can be formed, for example, from bovine, porcine, equine, ovine and/or other suitable animal tissues. The valve structure can be formed from heart valve tissue, pericardium, and/or other suitable tissue. In some embodiments, the valve structure can include or form one or more leaflets. For example, the valve structure can be in the form of a tri-leaflet bovine pericardium valve, a bi-leaflet valve, or another suitable valve.

A valve prosthesis is often packaged in a container filled with solution, such as glutaraldehyde, for sterilizing and preserving the valve prosthesis prior to attachment to a delivery device for delivery to a patient. Such a method is generally referred to as a "wet" stored valve. Sometimes, the valve prosthesis is preloaded on a distal portion of the delivery device, which are both packaged in the container. Some known packaging configurations include both wet and dry compartments; wherein the valve prosthesis is stored in a wet compartment loaded onto the delivery device component and the remainder of the delivery device component is secured in a dry compartment.

The disclosed embodiments address problems and limitations with the related art.

SUMMARY

It has been found that adequate sterilization of "wet" stored or packaged prosthetic heart valves or other implants, preloaded onto at least a first portion of an elongated delivery device, can be problematic as there are difficulties in sterilizing the device proximate one or more seals retaining sterilization fluid within a container containing the prosthetic heart valve. Disclosed assemblies provide "wet" packaging for a prosthetic heart valve with the first portion of a delivery device as well as methods of sterilizing a packaged prosthetic heart valve. Various disclosed assemblies include a container in which the prosthetic heart valve can be positioned preloaded on the first portion of a delivery device. The container is made of a non-porous material to retain sterilization fluid (e.g., glutaraldehyde). In some embodiments, the container includes an aperture in which a seal is formed between the delivery device and the container at a first, more proximal position with respect to the prosthetic heart valve. Then the packaged prosthetic heart valve can be sterilized with sterealizing fluid or the like in a first sterilization process. Next, the seal is removed and a second seal is formed between the container and the delivery device at a location more distal to the first position of the seal in preparation for a second sterilization process that will provide sterilization at the first position. The first and second seals can be either formed by the same or different seal members.

Alternate assemblies include an implant loaded onto a first portion of an elongated delivery device, a storage container including a first section and a second section; wherein the implant is positioned within the first section and the first portion of the delivery device is positioned in both the first and second sections, a first seal positioned to retain sterilization fluid within the first section; and a second seal positioned between the first portion of the delivery device and the second section. To sterilize such an assembly, the first and second portions can at least partially be filled with sterilizing solution. The first section can then be sealed to prevent escape of the sterilizing solution until the implant is to be delivered. The sterilization fluid within the second section can be drained after the second section is sterilized. Then, the second section can be removed and yet a further sterilization process can be conducted to sterilize the assembly proximate the previous location of the second seal.

Alternately, the assembly can be configured to include a first section and a second section interconnected by gas-permeable but liquid tights seals. The first section, which houses the implant, can be filled with sterilization fluid to sterilize the interior of the first section and can also prevent portions of the implant (e.g., valve tissue) from drying out. Ethylene oxide sterilization or the like can be used in a second sterilization process to sterilize the rest of the assembly, including areas proximate or adjacent the gas-permeable by liquid tights seals.

BRIEF DESCRIPTION OF THE DRAWINGS

FIG. 8A is an enlarged schematic illustration of a joining seal of FIG. 5 in a disengaged position.

FIG. 8B is an enlarged schematic illustration of the joining seal of FIGS. 5 and 8A in an engaged position.

FIG. 9 is an enlarged, schematic illustration of a complimentary receiver that can be selectively engaged with the joining seal of FIGS. 8A-8B.

FIG. 10 is an enlarged, schematic illustration of a lid of the assembly of FIG. 5.

FIG. 25A is a partial, cross-sectional view of the assembly of FIGS. 23-24.

FIGS. 25B-25C are partial, enlarged cross-sectional views of FIG. 25A.

FIG. 25D is an exploded view of the assembly of FIG. 25A.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted prosthetic heart valve, the terms "distal" and "outflow" are understood to mean downstream to the direction of blood flow, and the terms "proximal" or "inflow" are understood to mean upstream to the direction of blood flow.

As referred to herein, stented transcatheter prosthetic heart valves useful with and/or as part of the various systems, devices and methods of the present disclosure may assume a wide variety of different configurations, such as a bioprosthetic heart valve having tissue leaflets or a synthetic heart valve having polymeric, metallic or tissue-engineered leaflets, and can be specifically configured for replacing any of the four valves of the human heart. Thus, the stented prosthetic heart valve useful with the systems, devices, and methods of the present disclosure can be generally used for replacement of a native aortic, mitral, pulmonic or tricuspid valve, or to replace a failed bioprosthesis, such as in the area of an aortic valve or mitral valve, for example.

In general terms, the stented prosthetic heart valves of the present disclosure include a stent or stent frame having an internal lumen maintaining a valve structure (tissue or synthetic), with the stent frame having a normal, expanded condition or arrangement and collapsible to a compressed condition or arrangement for loading within a delivery device. The stent frame is normally constructed to self-deploy or self-expand when released from the delivery device. For example, the stents or stent frames are support structures that comprise a number of struts or wire segments arranged relative to each other to provide a desired compressibility and strength to the prosthetic heart valve. The struts or wire segments are arranged such that they are capable of self-transitioning from a compressed or collapsed condition to a normal, radially expanded condition. The struts or wire segments can be formed from a shape memory material, such as a nickel titanium alloy (e.g., nitinol). The stent frame can be laser-cut from a single piece of material, or can be assembled from a number of discrete components.

Figure 1A:
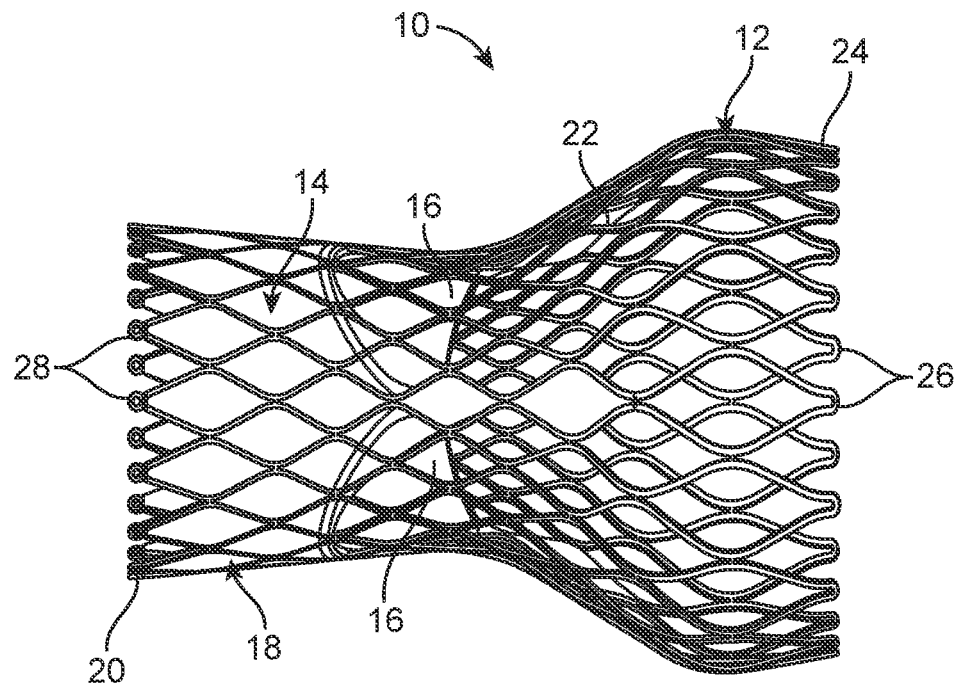
FIG. 1A is a side view of a stented prosthetic heart valve useful with systems, devices and methods of the present disclosure and in a normal, expanded condition.
Figure 1B:
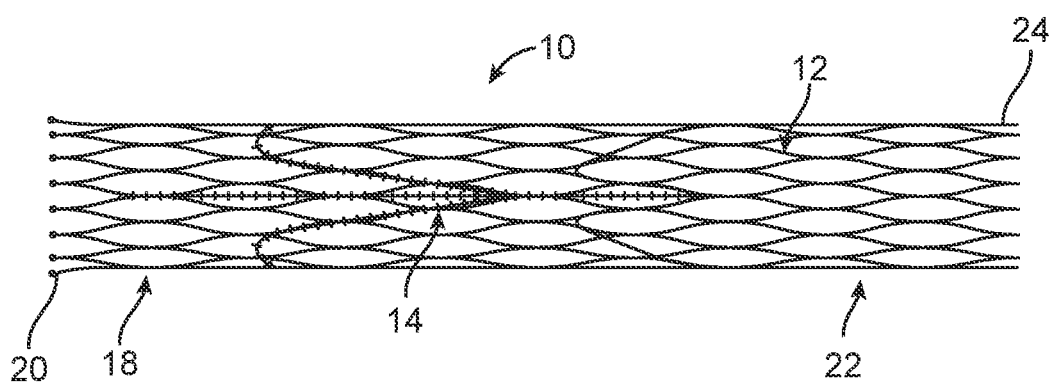
FIG. 1B is a side view of the prosthetic heart valve of FIG. 1A in a compressed condition.

With the above understanding in mind, one simplified, non-limiting example of a stented prosthetic heart valve 10 useful with systems, devices and methods of the present disclosure is illustrated in FIG. 1A. As a point of reference, the prosthetic heart valve 10 is shown in a normal or expanded condition in the view of FIG. 1A; FIG. 1B illustrates the prosthetic heart valve in a compressed condition (e.g., when compressively retained within an outer catheter or sheath as described below). The prosthetic heart valve 10 includes a stent or stent frame 12 and a valve structure 14. A paravalvular leakage prevention wrap (not shown) can also be provided around the stent frame 12. The stent frame 12 can assume any of the forms mentioned above, and is generally constructed so as to be self-expandable or balloon-expandable from the compressed condition (FIG. 1B) to the normal, expanded condition (FIG. 1A). In some embodiments, the stent frame can be balloon expandable or expanded mechanically.

The valve structure 14 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 14 can be formed, for example, from bovine, porcine, equine, ovine and/or other suitable animal tissues. In some embodiments, the valve structure 14 can be formed, for example, from heart valve tissue, pericardium, and/or other suitable tissue. In some embodiments, the valve structure 14 can include or form one or more leaflets 16. For example, the valve structure 14 can be in the form of a tri-leaflet valve, a bi-leaflet valve, or another suitable valve. In some constructions, the valve structure 14 can comprise two or three leaflets that are fastened together at enlarged lateral end regions to form commissural joints, with the unattached edges forming coaptation edges of the valve structure 14. The leaflets 16 can be fastened to a skirt that in turn is attached to the frame 12. The upper ends of the commissure points can define an inflow portion 18 corresponding to a first or inflow end 20 of the prosthetic heart valve 10. The opposite end of the valve can define an outflow portion 22 corresponding to a second or outflow end 24 of the prosthetic heart valve 10. As shown, the stent frame 12 can have a lattice or cell-like structure, and optionally forms or provides crowns 26 and/or eyelets 28 (or other shapes) at the outflow and inflow ends 20, 24.

With the one exemplary construction of FIGS. 1A and 1B, the prosthetic heart valve 10 can be configured (e.g., sized and shaped) for replacing or repairing an aortic valve. Alternatively, other shapes are also envisioned, adapted to mimic the specific anatomy of the valve to be repaired (e.g., stented prosthetic heart valves useful with the present disclosure can alternatively be shaped and/or sized for replacing a native mitral, pulmonic or tricuspid valve or compassionate use such as heterotopic implants).

Figure 2A:
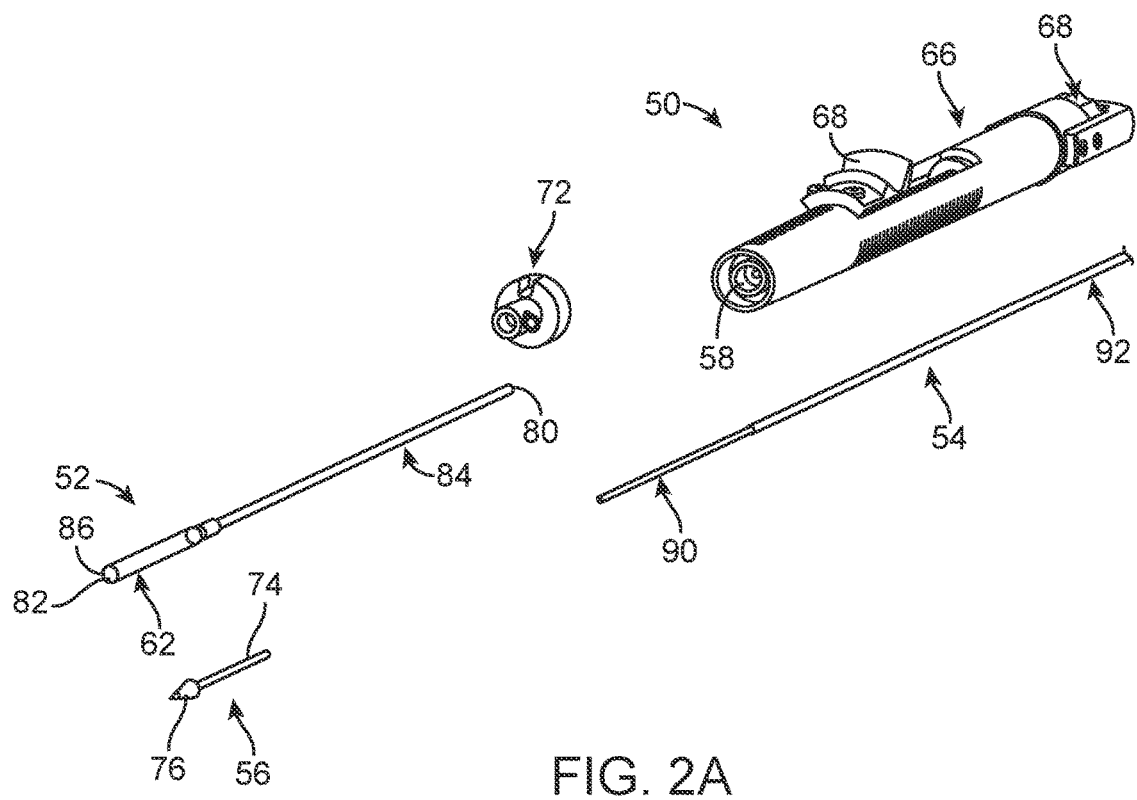
FIG. 2A is an exploded perspective view of a stented prosthetic heart valve delivery device in accordance with principles of the present disclosure.
Figure 2B:
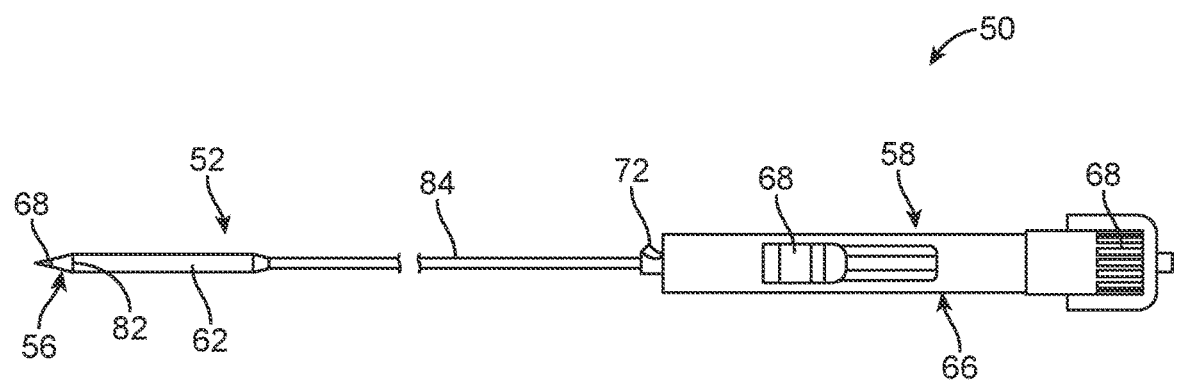
FIG. 2B is an assembled top view of the stented prosthetic heart valve delivery device of FIG. 2A.

With the above understanding of the stented prosthetic heart valves in mind, one embodiment of a delivery device 50 for percutaneously delivering the prosthesis or an alternate implant is shown in simplified form in FIGS. 2A and 2B. The delivery device 50 includes a delivery sheath assembly 52, an inner shaft assembly 54, a spindle 56 and a handle assembly 58. Details on the various components are provided below. In general terms, however, the delivery device 50 combines with a stented prosthetic heart valve (e.g., the prosthetic heart valve of FIGS. 1A-1B) to form a system for performing a therapeutic procedure on a defective heart valve of a patient. The delivery device 50 provides a loaded or delivery state in which a stented prosthetic heart valve is loaded over the spindle 56 and is compressively retained within a capsule 62 of the delivery sheath assembly 52. The delivery sheath assembly 52 can be manipulated to withdraw the capsule 62 proximally from over the prosthetic heart valve via operation of the handle assembly 58, permitting the prosthetic heart valve to self-expand and partially release from the spindle 56. When the capsule 62 is retracted proximally beyond the valve retainer (not shown), the stented prosthetic heart valve can completely release or deploy from the delivery device 50. The delivery device 50 can optionally include other components that assist or facilitate or control complete deployment, as desired.

Various features of the components 52-58 reflected in FIGS. 2A and 2B and as described below can be modified or replaced with differing structures and/or mechanisms. Thus, the present disclosure is in no way limited to the delivery sheath assembly 52, the inner shaft assembly 54, the spindle 56 or the handle assembly 58 as shown and described below. Any construction that generally facilitates compressed loading of a stented prosthetic heart valve over an inner shaft via a retractable outer sheath or capsule is acceptable. Further, the delivery device 50 can optionally include additional components or features, such as a flush port assembly 72, a recapture sheath (not shown), etc.

In some embodiments, the delivery sheath assembly 52 defines proximal and distal ends 80, 82, and includes the capsule 62 and an outer shaft 84. The delivery sheath assembly 52 can be akin to a catheter, defining a lumen 86 (referenced generally) that extends from the distal end 82 through the capsule 62 and at least a portion of the outer shaft 84. The lumen 86 can be open at the proximal end 80 (e.g., the outer shaft 84 can be a tube). The capsule 62 extends distally from the outer shaft 84, and in some embodiments has a more stiffened construction (as compared to a stiffness of the outer shaft 84) that exhibits sufficient radial or circumferential rigidity to overtly resist the expected expansive forces of the stented prosthetic heart valve (not shown) when compressed within the capsule 62. For example, the outer shaft 84 can be a polymer tube embedded with a metal braiding, whereas the capsule 62 includes a laser-cut metal tube that is optionally embedded within a polymer covering. Alternatively, the capsule 62 and the outer shaft 84 can have a more uniform or even homogenous construction (e.g., a continuous polymer tube). Regardless, the capsule 62 is constructed to compressively retain the stented prosthetic heart valve at a predetermined diameter when loaded within the capsule 62, and the outer shaft 84 serves to connect the capsule 62 with the handle assembly 58. The outer shaft 84 (as well as the capsule 62) is constructed to be sufficiently flexible for passage through a patient's vasculature, yet exhibits sufficient longitudinal rigidity to effectuate desired axial movement of the capsule 62. In other words, proximal retraction of the outer shaft 84 is directly transferred to the capsule 62 and causes a corresponding proximal retraction of the capsule 62. In other embodiments, the outer shaft 84 is further configured to transmit a rotational force or movement onto the capsule 62.

The inner shaft assembly 54 can have various constructions appropriate for supporting the delivery sheath assembly 52, including indirectly supporting the spindle 56 (and a stented prosthetic heart valve disposed thereon) relative to the capsule 62. In some embodiments, the inner shaft assembly 54 includes an intermediate shaft or tube 90 and a proximal shaft or tube 92. The intermediate tube 90 is optionally formed of a flexible polymer material (e.g., PEEK), and is sized to be slidably received within the delivery sheath assembly 52. The intermediate tube 90 serves as a transition to the deflection assembly 60, and in some embodiments is a flexible polymer tubing (e.g., PEEK) having a diameter slightly less than that of the proximal tube 92. The proximal tube 92 can have a more rigid construction, configured for robust assembly with the handle assembly 58, such as a metal hypotube. Other constructions are also envisioned. For example, in other embodiments, the intermediate and proximal tubes 90, 92 are integrally formed as a single, homogenous tube or shaft. Regardless, the inner shaft assembly 54 forms or defines at least one lumen (not shown) sized, for example, to slidably receive a guide wire (not shown).

The spindle 56 includes an inner support shaft 74 and a tip 76. The inner support shaft 74 is sized to be slidably received within the lumen 86 of the delivery sheath assembly 52, and is configured for mounting to the deflection assembly 60. The inner support shaft 74 can be a flexible polymer tube embedded with a metal braid. Other constructions are also acceptable so long as the inner support shaft 74 exhibits sufficient structural integrity to support a loaded, compressed stented prosthetic heart valve or other implant (not shown). The tip 76 forms or defines a nose cone having a distally tapering outer surface adapted to promote atraumatic contact with bodily tissue. The tip 76 can be fixed or slidable relative to the inner support shaft 74. The spindle 56 can define a continuous lumen (not shown) sized to slidably receive an auxiliary component such as a guide wire (not shown).

The handle assembly 58 generally includes a housing 66 and one or more actuator mechanisms 68 (referenced generally). The housing 66 maintains the actuator mechanism(s) 68, with the handle assembly 58 configured to facilitate sliding movement of the delivery sheath assembly 52 relative to other components (e.g., the inner shaft assembly 54, the spindle 56). The housing 66 can have any shape or size appropriate for convenient handling by a user.

With the above general explanations of exemplary embodiments of the components 52-58 in mind, the present disclosure provides many assemblies for storing prosthetic heart valves in a "wet" (generally submerged within sterilization fluid) state either with or without part of a delivery device (e.g., the spindle 56 of the delivery device 50). The disclosed embodiments are configured to allow for sterilization of the assembly. In the embodiments disclosed herein, the prosthetic heart valves can either be stored in either the expanded or compressed condition.

Figure 3A:
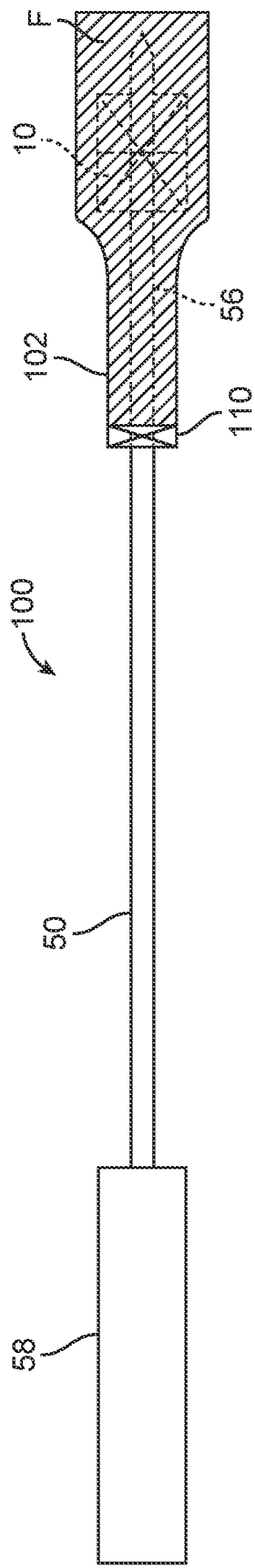
FIG. 3A is a schematic illustration of an assembly in a first configuration for a first sterilization process in which a seal is formed in a first location.
Figure 3B:
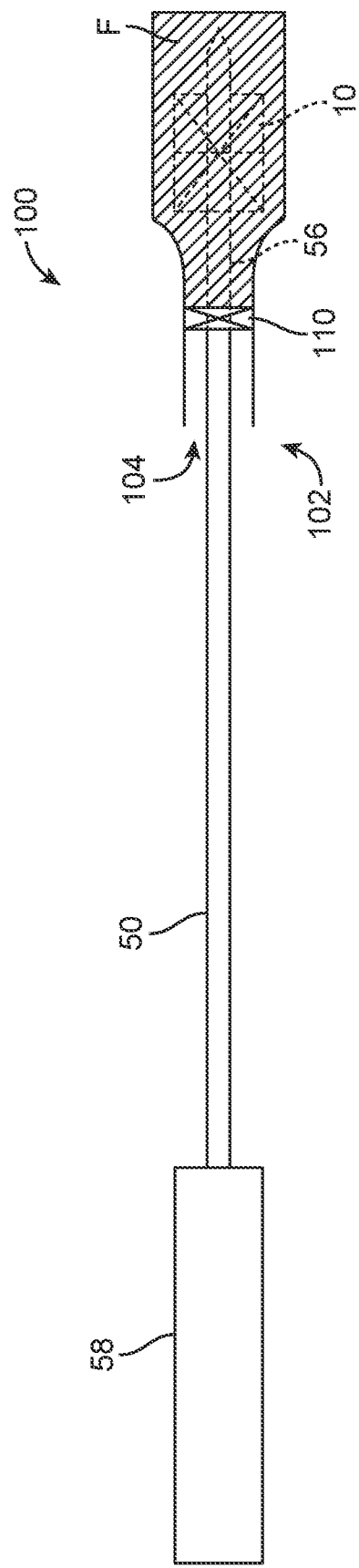
FIG. 3B is a schematic illustration of the assembly of FIG. 3A in a second configuration for a second sterilization process in which a seal is formed in a second location.

One embodiment of an assembly 100 is illustrated in FIGS. 3A-3B. In this embodiment, an implant such as a prosthetic heart valve 10 is loaded onto a first portion of the delivery device (e.g., the spindle 56). It is to be understood that the delivery device of FIGS. 2A-2B is schematically shown in this embodiment only as an example and other types of delivery devices can be used with the disclosed assemblies and methods. In this embodiment, the prosthetic heart valve 10 is loaded onto and packaged with a complete delivery device 50, however, not all of the delivery device is required as part of the assembly. For example, the handle assembly 58 or other, perhaps reusable, components of the delivery device 50 can be omitted and put together prior to use. In one example embodiment, the assembly 100 can include only the spindle 56 of the delivery device 50. The assembly 100 further includes a storage container 102 including an opening 104 through which a prosthetic heart valve 10 can be inserted. The storage container 102 is made of non-porous material (e.g., glass, film). The assembly 100 further includes at least one seal member 110, which can be used to retain sterilization fluid F (e.g., glutaraldehyde or the like) within the storage container 102.

Figure 4:
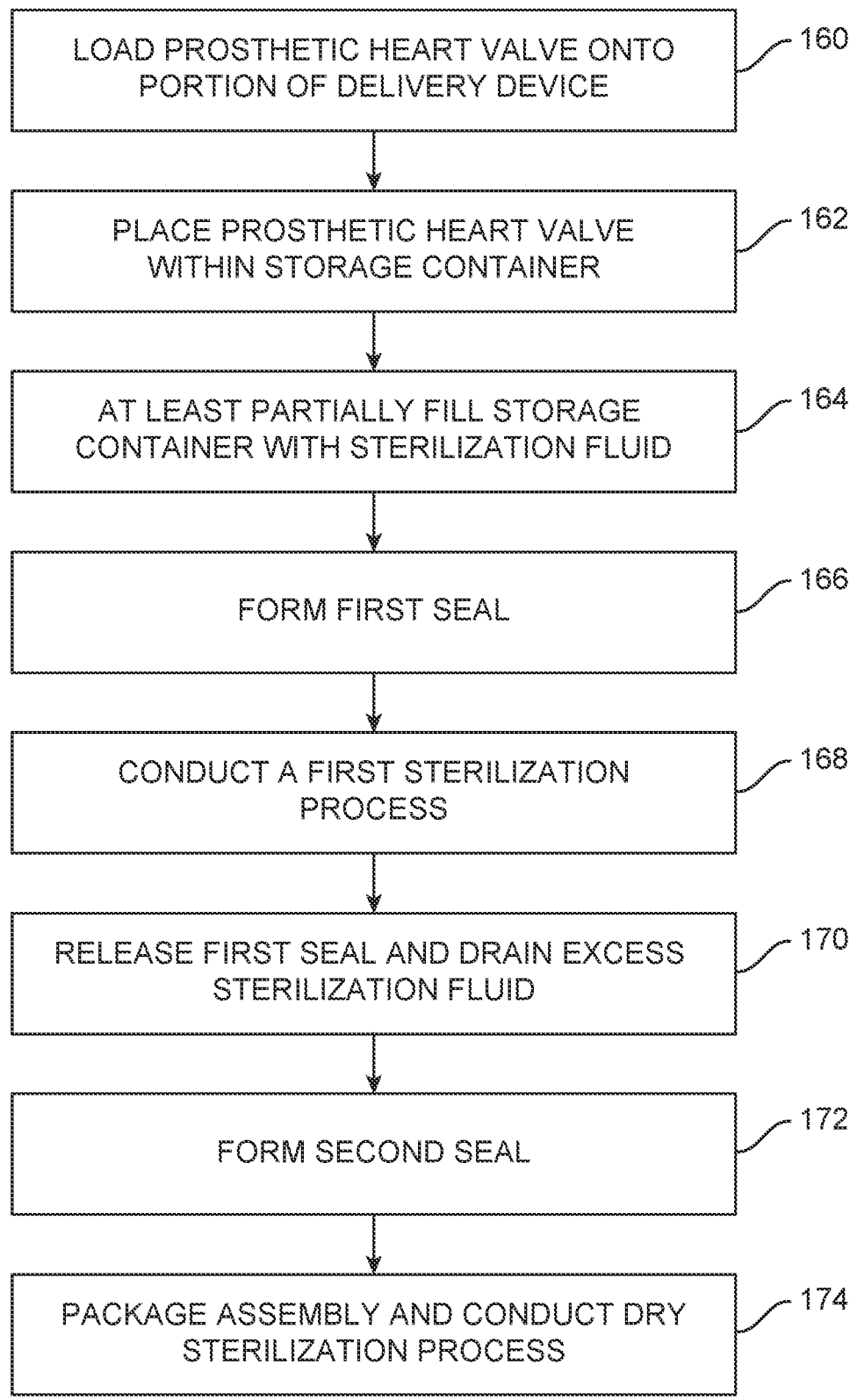
FIG. 4 is a flow chart of a method of sterilizing the assembly of FIGS. 3A-3B.
Figure 5:
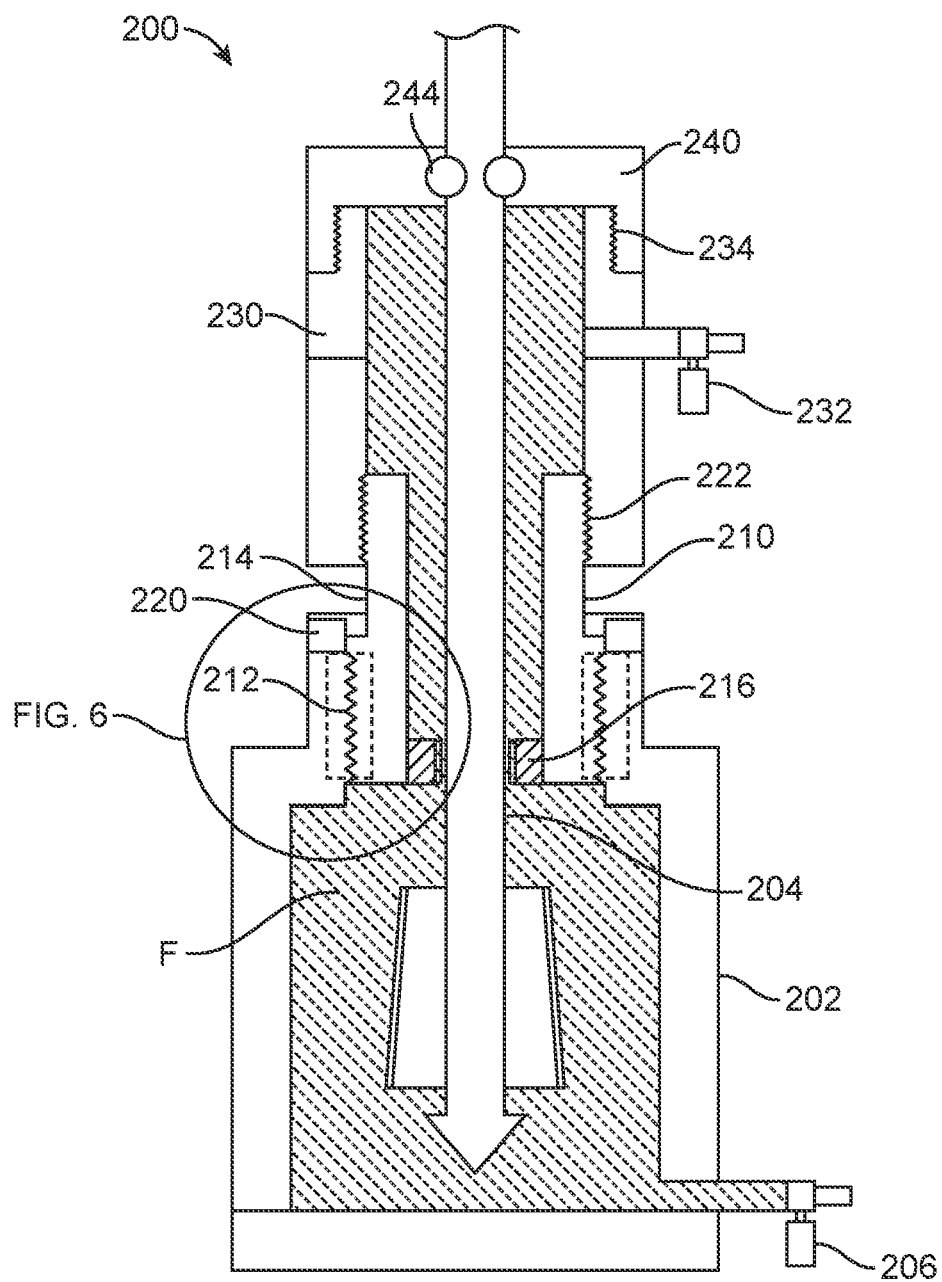
FIG. 5 is a schematic illustration of an alternate assembly.
Figure 6:
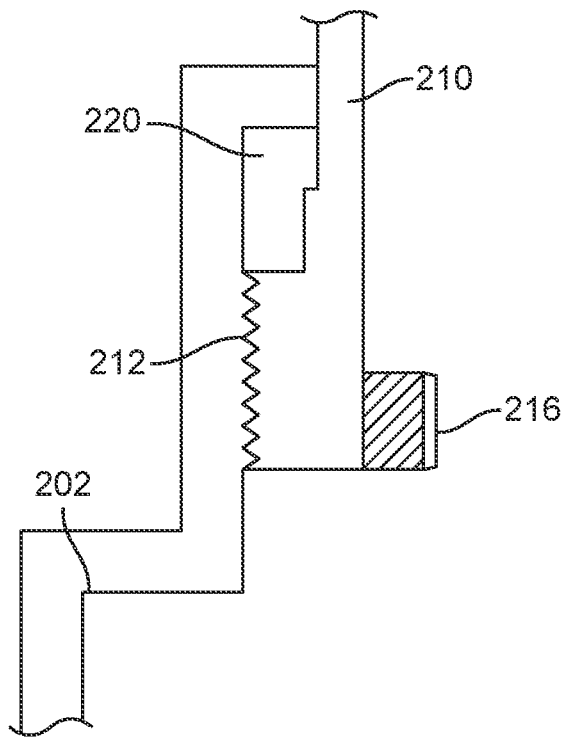
FIG. 6 is an enlarged schematic illustration of the assembly of FIG. 5.
Figure 7:
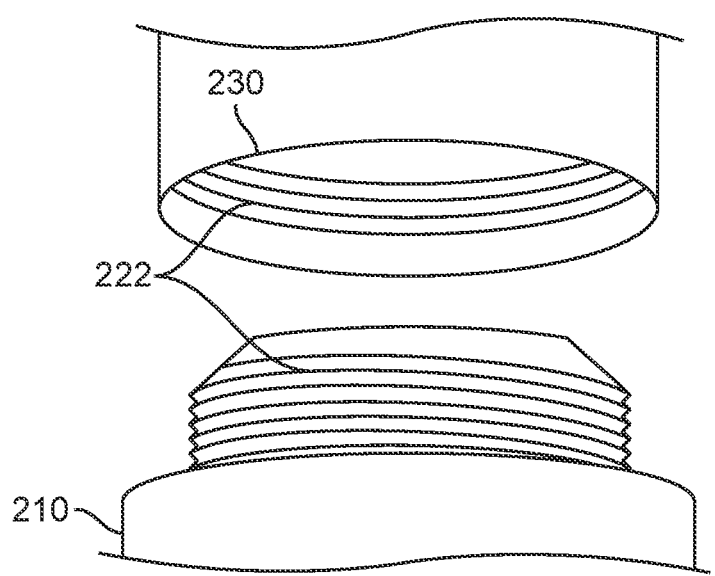
FIG. 7 is an enlarged schematic illustration of the assembly of FIG. 5.

One example method of sterilizing the assembly 100 is generally outlined in FIG. 4. After the prosthetic heart valve is loaded onto at least a portion of a delivery device 160, the prosthetic heat valve is positioned within the storage container 162 and the storage container is at least partially filled with sterilization fluid (e.g., glutaraldehyde or the like) 164. The first seal is formed with the seal member at a first position in the opening to retain the sterilization fluid within the storage container 166. The sterilization fluid sterilizes the prosthetic valve and areas inside of the storage container 168 as well as provides moisture beneficial for tissue of the valve structure. The method further comprises the step of releasing the first seal from the first position 170, optionally draining excess sterilization fluid from within the storage container 170 and forming a second seal at a second position that is distal with respect to the first position 172. In other words, the second position is closer to the prosthetic heart valve as compared to the first position. Then, the assembly is packaged in a sealed pouch and a dry sterilization process is conducted either via gas-based or radiation-based sterilization techniques 174, for example. This dry sterilization process 174 sterilizes the areas of concern proximate the first position where the first seal was previously formed at step 166 as well as other areas of the assembly outside of the storage container.

The "dry" sterilization techniques discloses herein, include, but are not limited to, gas-based techniques known in the art such as ethylene oxide (EtO). Such "dry" sterilization techniques also include radiation-based sterilization techniques including, but not limited to electron beam sterilization.

The seal member 110 can include heat shrink wrap or mechanical seal. If a mechanical seal, the seal member 110 can be formed by repositioning the seal member 110. In other embodiments, the first and second seals can be formed be formed by different seal members.

A second assembly 200 is schematically illustrated in FIGS. 5-10. The assembly 200 includes the first portion of the delivery device, such as the spindle 56 disclosed above, for example. Loaded to the spindle 56 is an implant, such as the prosthetic heart valve 10. The loaded prosthetic heart valve 10 is positioned within a storage container 202. The storage container 202 includes an opening 204 for receiving the loaded prosthetic heart valve 10 and is made of a non-permeable material, such as glass or plastic. The storage container 202 further includes a stop cock 206 or other mechanism for providing a closeable/openable conduit from the exterior of the storage container 202 to the inside of the storage container 202 proximate the implant 10. The stop cock 206 is used for filling and draining sterilization fluid as will be discussed in further detail below.

The assembly 200 further includes a sealing piece 210 that can be removably connected to the storage container 202 via a threaded connection 212 (generally referenced). The sealing piece 210 includes a body 214 made of a non-porous material and a joining seal 216 configured to both secure the sealing piece 210 to the storage container 202 and create a liquid-tight seal between the body 214, the spindle 56 and the storage container 202 proximate the opening 204. In one optional embodiment, the joining seal 216 can be of the type illustrated in FIGS. 8A-8B, which includes a plurality of prongs 218 that are biased outwardly from a central axis A of the joining seal 216 similar to what can be used for garden hose fittings. Rotation of the joining seal 216 in either a clockwise or counterclockwise direction can either engage or disengage the prongs 218 (only a few of which are referenced in FIG. 8A-8B) with the storage container 202 when the storage container 202 is configured to include an appropriate receiver to accept such a joining seal 216 (see, e.g., FIG. 9 which illustrates one example of an appropriate receiver 208, which is of the type used in garden hose fittings, as is shown in FIG. 9). In some embodiments, the storage container 202 overlaps at least part of the sealing piece 210 adjacent the joining seal 216. The storage container 202 can additionally include a feature 220 that ensures that a nonsterile surface of the joining seal 216 cannot be contacted during use.

Attached to the sealing piece 210 via a threaded connection 222 (generally referenced, see also FIG. 7) is a sterilization container 230 that is also made of a non-porous material. The sterilization container 230 is connected to a lid 240. The lid 240 includes an aperture 242 for receiving the spindle 56 and also a seal 244 circumscribing the aperture 242 to form a liquid-tight seal between the lid 240 and the spindle 56. In some embodiments, the lid 240 can be provided in two interlocking pieces 246a, 246b that can be connected around and disconnected from around the spindle 56. The sterilization container 230 can further include a stopcock 232 or other mechanism for providing a closeable conduit from the exterior of the assembly 200 to the inside of the assembly 200. The sterilization container 230 and lid 240 can include corresponding threads 234 (jointly referenced) for enabling a threaded connection between both the sterilization container 230 and the lid 240.

Figure 11:
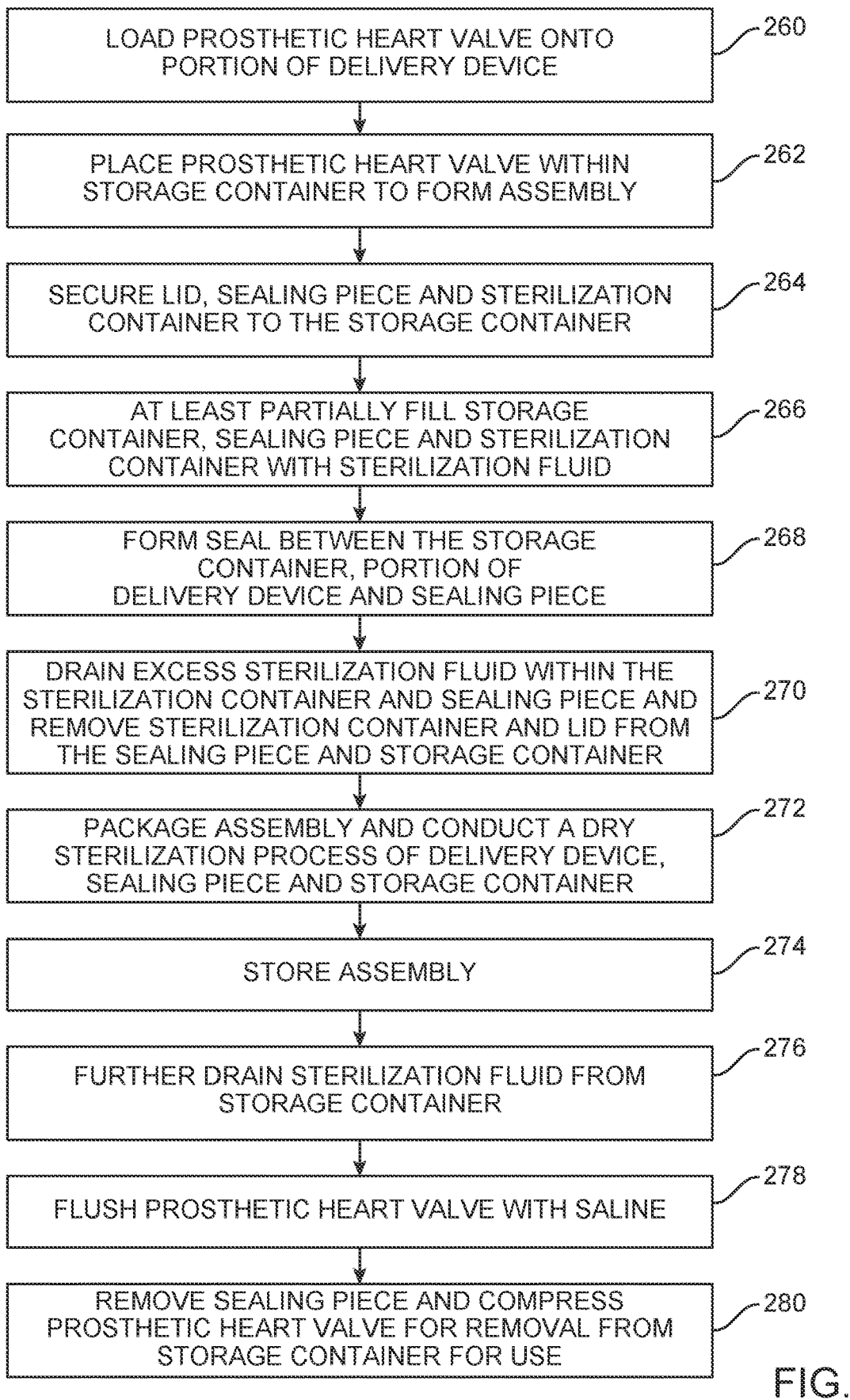
FIG. 11 is a flow chart of a method of sterilizing the assembly of FIG. 5.
Figure 12B:
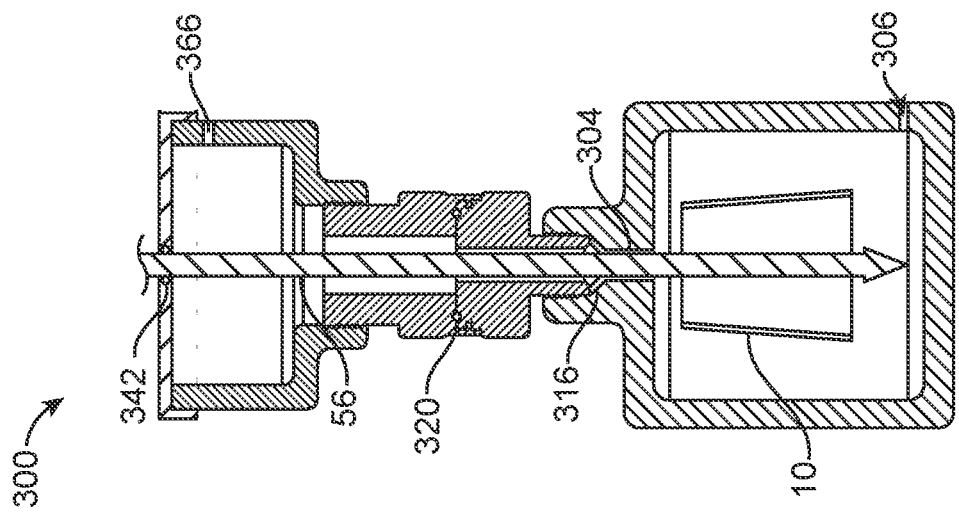
FIG. 12B is a cross-sectional view of the assembly of FIG. 12A.
Figure 12A:
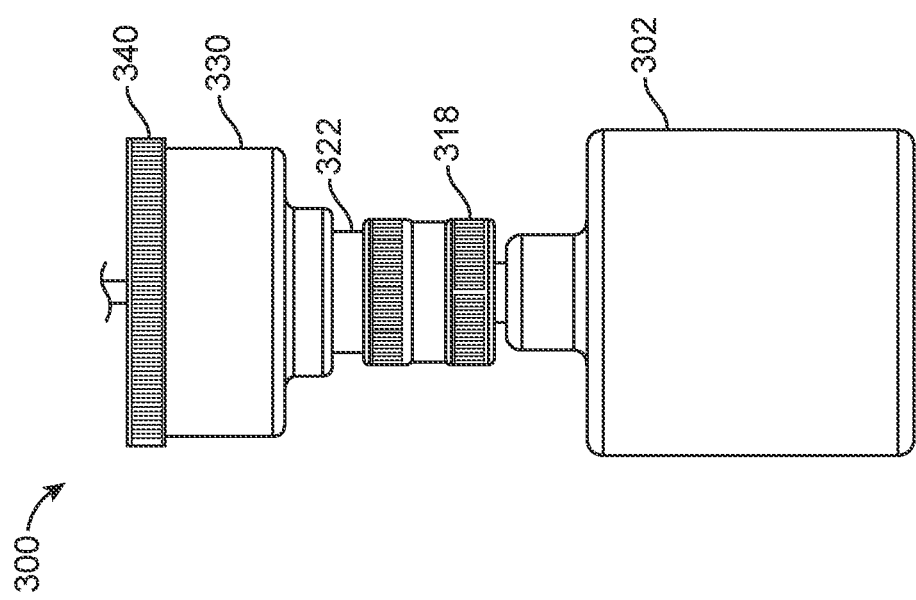
FIG. 12A is a front view of an alternate assembly.

One method of sterilizing the assembly of FIGS. 5-10 is generally illustrated in the flow chart of FIG. 11. In this method, prosthetic heart valve or other implant is loaded onto a first portion of the delivery device 260, such as the spindle as disclosed above. The prosthetic heart valve is placed within storage container to form an assembly 262. The sealing piece, sterilization container, lid and sealing piece are secured to the storage container 264 in the arrangement illustrated in FIG. 5. Then, the storage container, sealing piece and sterilization container are at least partially filled with sterilization fluid, such as glutaraldehyde, via one or both of the stop cocks 266. After the sterilization fluid sufficiently sterilizes the interior of the storage container, portion of the delivery device, the sealing piece and sterilization container, a seal is formed between the storage container, portion of the delivery device and sealing piece 268, for example, by rotating the sealing piece to tighten the prongs of the joining seal against the storage container. Next, the sterilization fluid is drained from within the sterilization container and sealing piece 270. The sterilization container and lid are removed from the sealing piece and storage container 270. The assembly is then packed in a sealed pouch and then a dry sterilization process of the spindle (can also optionally include additional portions of a delivery device), sealing piece and storage container is conducted via gas-based or radiation-based sterilization techniques to sterilize the exterior of the assembly packaged within the sealed pouch 272. At this stage the assembly can be stored prior to use 274. At the time the assembly is to be used, the sterilization fluid is drained from the storage container 276 and saline is introduced through the stop cock of the storage container to flush prosthetic heart valve 278. The sealing piece is then removed and the prosthetic heart valve is compressed for removal from the storage container for use 280.

Referring now also to FIGS. 12A-22, which collectively illustrate yet another alternate assembly 300. The assembly 300 includes a storage container 302 made of a non-porous material. The storage container 302 includes an opening 304 for receiving a loaded prosthetic heart valve or implant 10. The storage container 302 also includes a stop cock port 306 for receiving a stopcock (not shown). Positioned within the opening 304 is a seal 316 that circumscribes the portion of the delivery device to which the prosthetic heart valve 10 is loaded. In the illustrated embodiment, the seal 316 provides a seal between the spindle 56 and the storage container 302 for retaining sterilization fluid (not shown) within the storage container 302. The assembly 300 further includes a first Tuohy Borst piece 318 and a second Tuohy Borst piece 322 both optionally having a textured outer surface for gripping by a user. Attached to the second Tuohy Borst piece 322 is a sterilization container 330 having a stop cock port 366 for receiving a stop cock (not shown; can be of the type illustrated in FIG. 5). Positioned over the sterilization container 330 proximate the seal 342 is a lid 340. The lid 340 can also include a textured outer surface for gripping by a user. A seal 342 interfaces between the spindle 56 and the lid 340.

Figure 13:
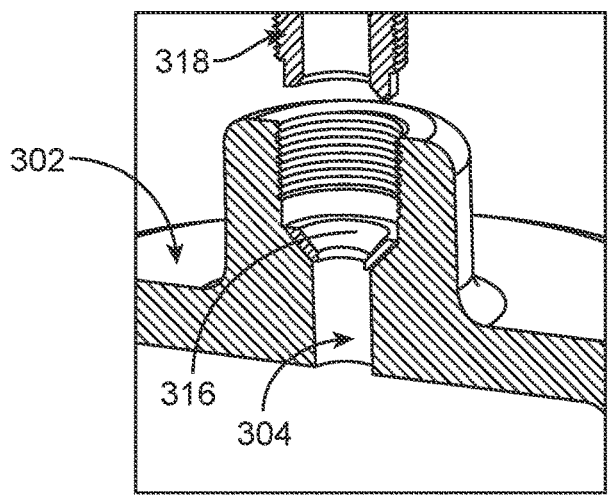
FIGS. 13-22 are cross-sectional views of the assembly of FIGS. 12A-12B in various stages of being put together.
Figure 14:
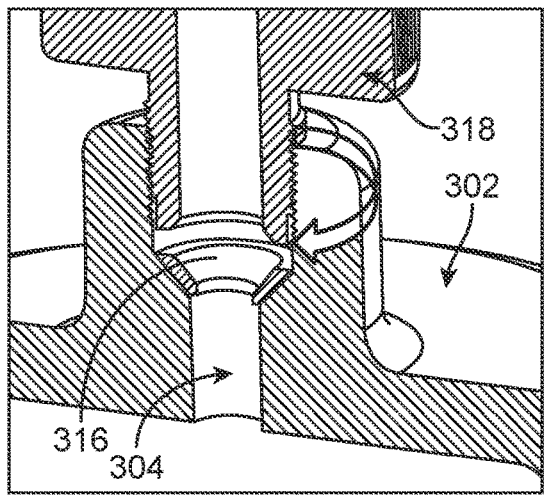
Figure 15:
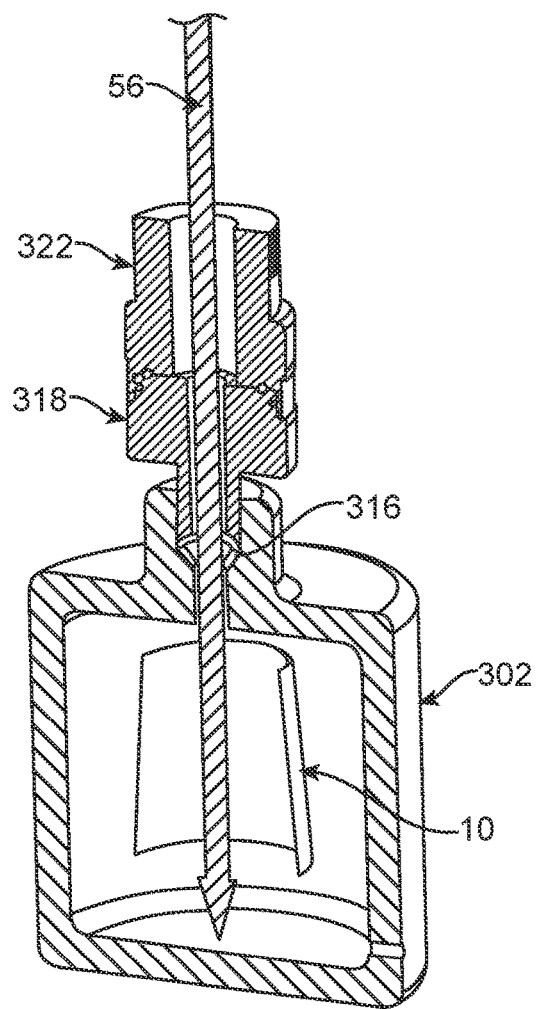
Figure 16:
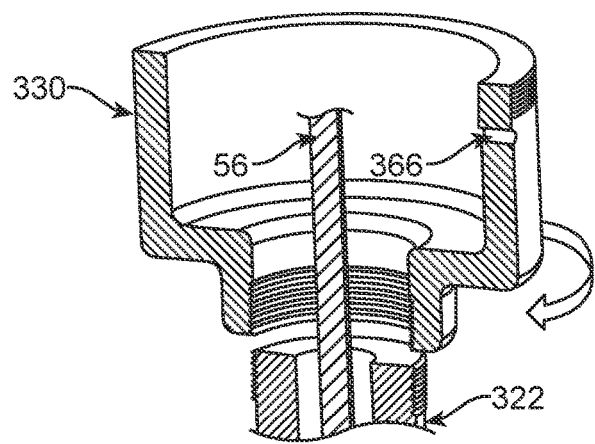
Figure 17:
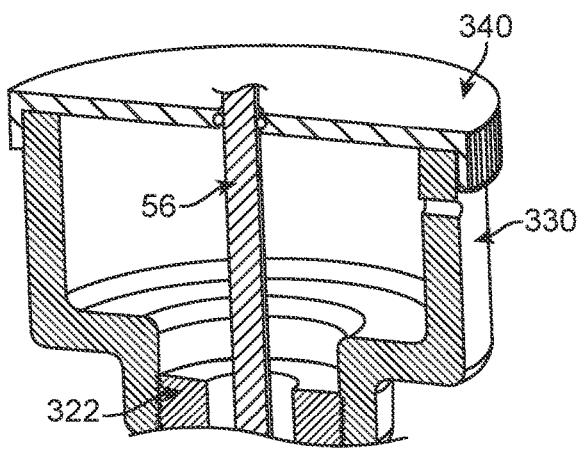
Figure 18:
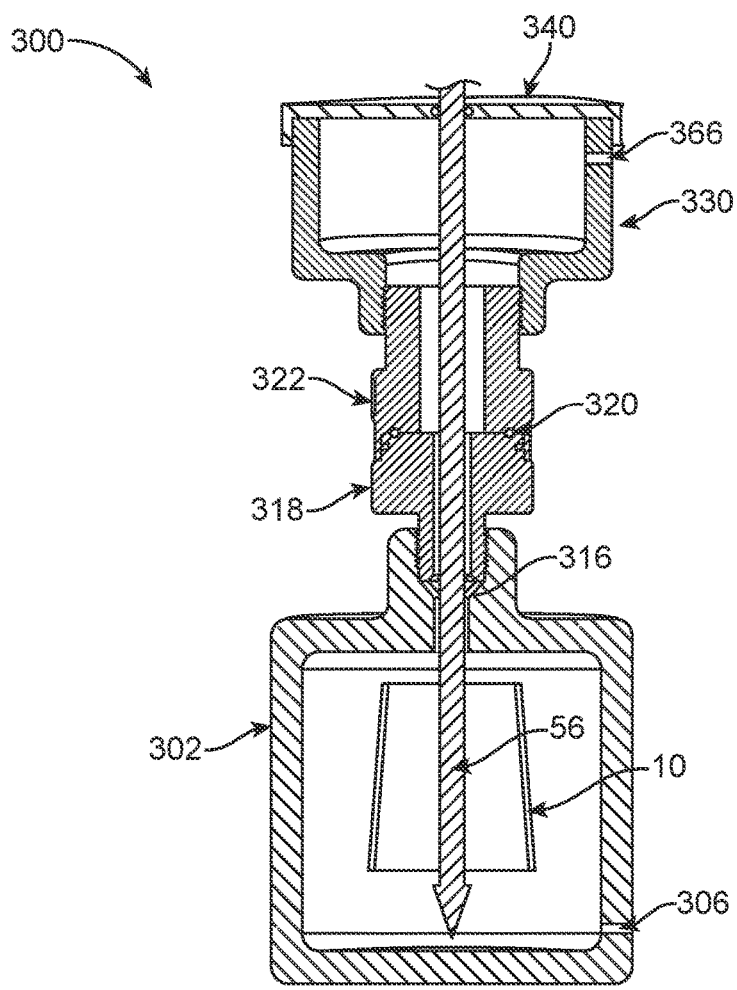
Figure 20:
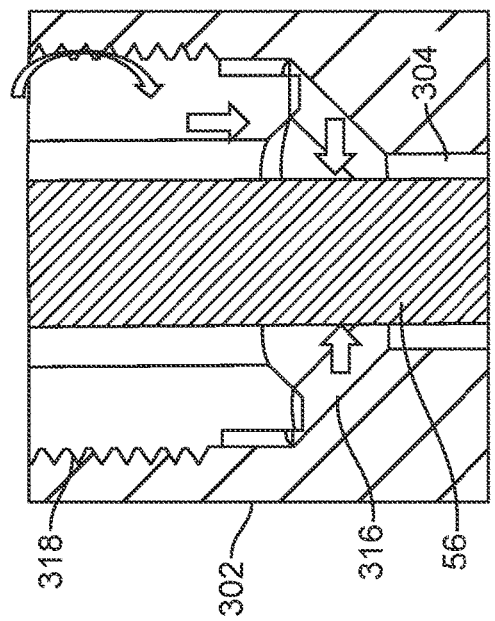

One method of sterilizing the assembly 300 can be summarized as follows. In such an example method the Tuohy Borst seal 316 can be positioned in placed as generally illustrated in FIG. 13 and the storage container 302 can be connected to the Tuohy Borst assembly 318, 320, 322 (FIGS. 14-15). Then, the implant 10 can be loaded onto the spindle 56 and then placed inside of the storage container 302 having the Tuohy Borst assembly 318, 320, 322 attached thereto as is generally depicted in FIG. 15. As shown in FIG. 15, the implant can then be deployed (expanded) within the storage container 302 to the point where the implant 10 can be reloaded using the delivery device later in time. Next, the sterilization container 330 is attached to the second Tuohy Borst piece 322 via threaded connection or the like (FIG. 16). The lid 340 can then be secured over the sterilization container 330 as shown in FIG. 17. The stop cock port 306 can receive a stop cock (not shown) that can be used to at least partially fill the assembly shown in FIG. 18 with sterilization fluid (not shown) of the types disclosed above. The stop cock port 366 can then be closed via the stopcock inserted therein to perform sterilization of the interior of the assembly 300 via contact with the sterilizing fluid.

Figure 19:
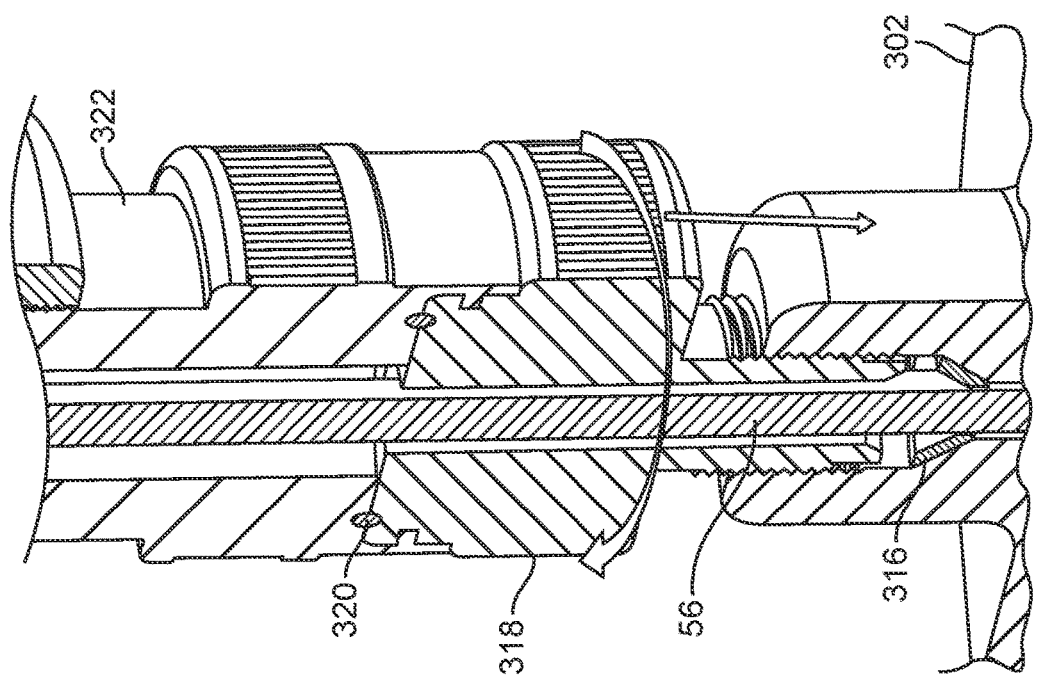

After sterilization of the interior of the assembly 300, the first Tuohy Borst piece 318 is rotated relative to the storage container 302 to drive the first Tuohy Borst piece 318 against the Tuohy Borst seal 316 as is generally depicted in FIG. 19. The downward motion of the first Tuohy Borst piece 318 will cause the seal 316 to compress against the spindle 56 creating a seal separating the sterilization fluid in the storage container 302 with the sterilization fluid in the proximal the seal 316. The seal/spindle interface of FIG. 20 will have exposure to the sterilization fluid at this stage, as will other interior portions of the assembly 300 distal to the seal 316.

Figure 21:
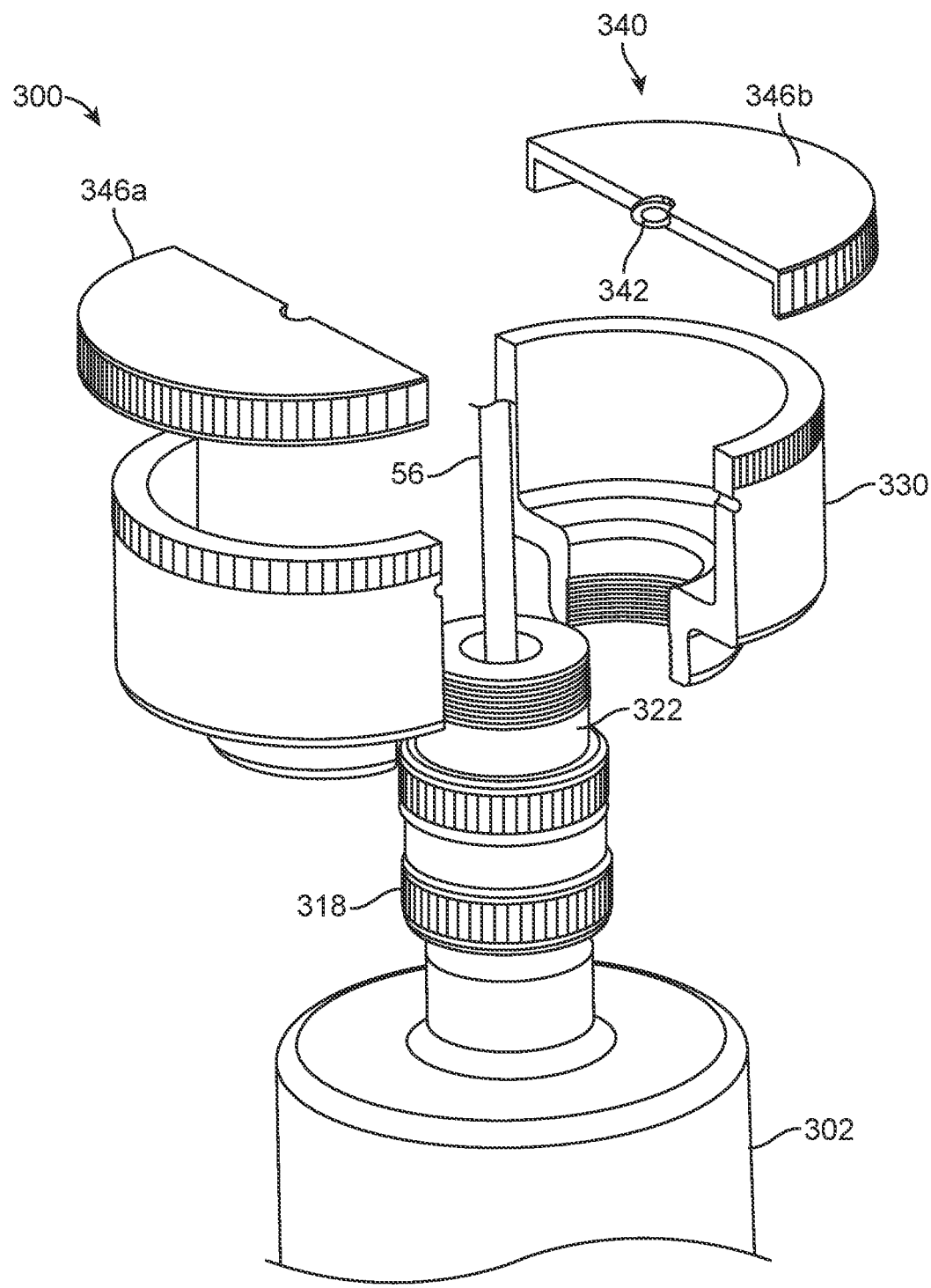
Figure 22:
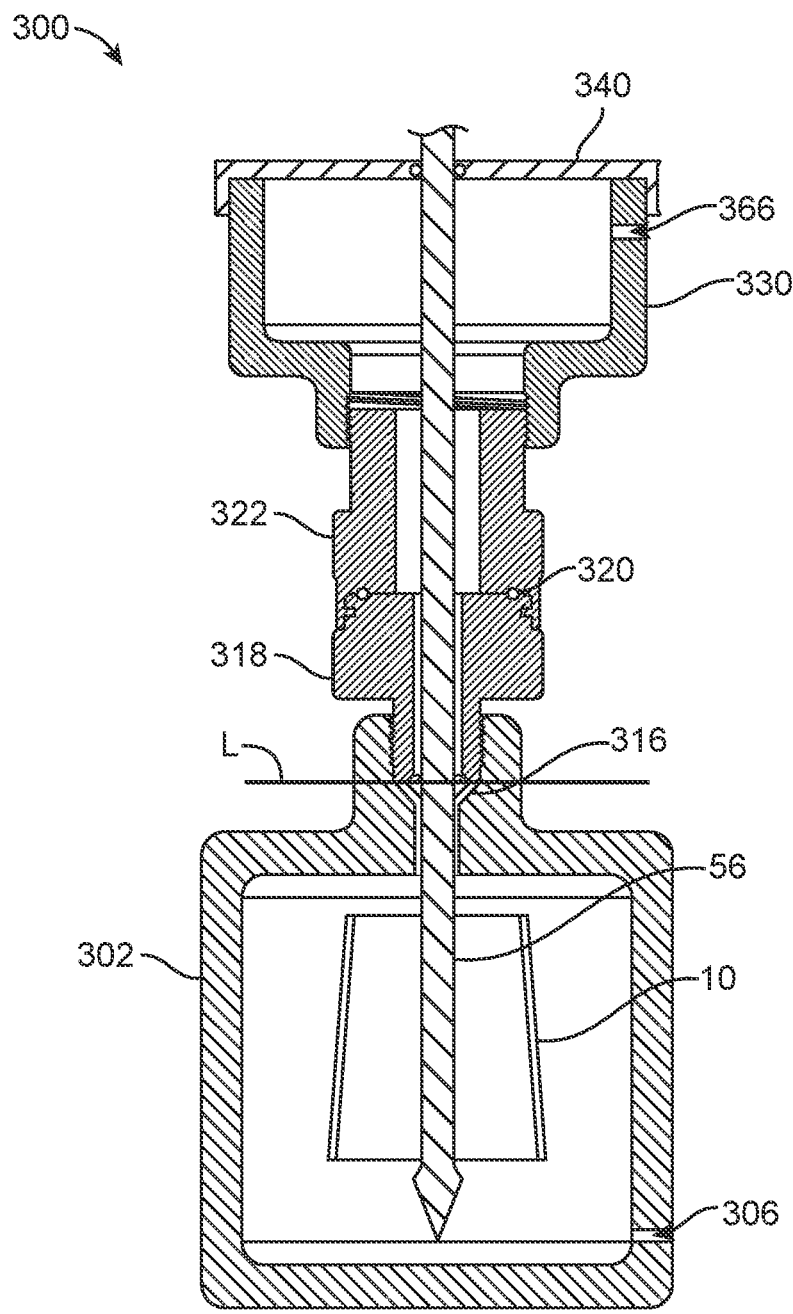

To sterilize additional portions of the assembly 300, the stop cock port 366 is opened and the sterilization fluid is drained from the sterilization container 330. The sterilization container 330 and lid 340 are removed via an optional two-piece 346a, 346b lid 340 configuration as shown in FIG. 21. At this point, everything distal to line L within the assembly 300 is sterile (FIG. 22). The assembly is the packaged in a sealed pouch and everything proximal to the line L and outer surfaces of the assembly 300 are next sterilized in a second "dry" sterilization process such as EtO sterilization, electron beam sterilization or the like. Once the assembly 300 is returned from the second sterilization process, the assembly 300 can be used by draining the remaining sterilization fluid via the stop cock port 306. The storage container 302 can be flushed with saline until the sterilization fluid is removed from the implant 10 or reduced to a desired level. The implant 10 can then be compressed. The Tuohy Borst seal assembly 318, 320, 322 is opened and the implant 10 is retracted from the storage container 302 loaded on the spindle 56.

Figure 23:
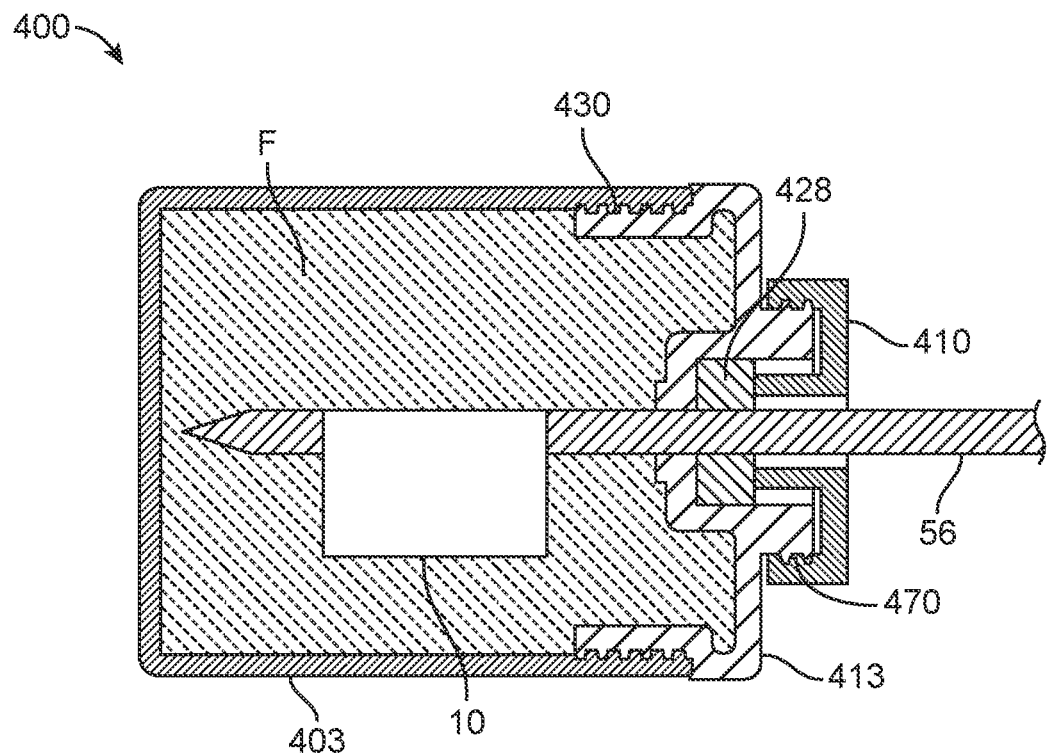
FIG. 23 is a cross-sectional view of yet another assembly.
Figure 24:
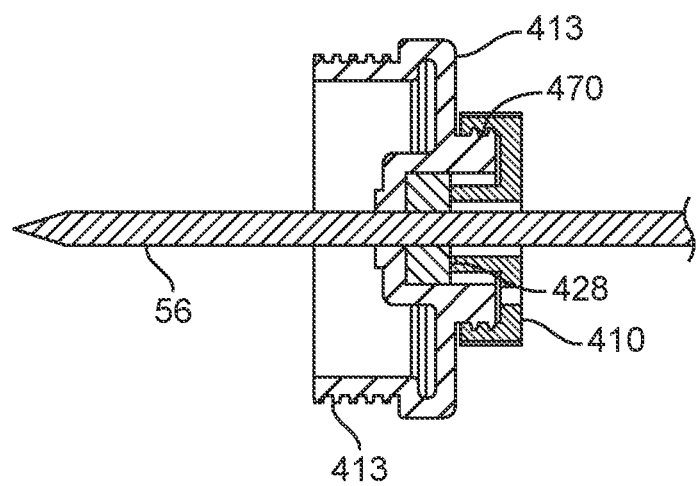
FIG. 24 is a partial, cross-sectional view of the assembly of FIG. 24.

Turning now also to FIGS. 23-25D, which collectively illustrate components of an alternate assembly 400 for storing a prosthetic heart valve or other implant 10 and a first portion of a delivery device (e.g., the spindle 56). The assembly 400 includes a container 402 made of a non-permeable material, such as one of those disclosed above, that can house the prosthetic heart valve loaded onto the portion of a delivery device. The container 402 can optionally include a vent (not visible) that has a high IP rating to retain sterilization fluid F within the container 402 but is suitable for "dry" gas-based or radiation-based sterilization techniques. The container 402 of this embodiment includes a first section 403 that can be selectively secured to a second section 413 via threading or the like. A removable cover 410 is connected to the second section 413. The lid 410 can be arranged and configured to screw on to the second section 413, for example when the assembly 400 is operatively assembled as is shown in FIGS. 23 and 25A and the spindle 56 is positioned within an aperture 424 formed by the lid 410, seal 428 and second section 413. The seal 428 can be an annulus made of rubber or similar material. In this embodiment, the assembly 400 can include one or more Tyvek® (flashspun high-density polyethylene fibers) seals 430, 470, 472 to form a liquid tight seal at joints between interconnected elements. For example, one Tyvek® seal 430 can optionally be provided at the threaded connection between the first section 403 and the second section 413. A second Tyvek® seal 470 can optionally be provided at the connection between the second section 413 and the lid 410. In addition, one Tyvek® seal 472 can optionally be provided between the second section 413 and the seal 428. The container 402 can be sterilized as sterilizing fluid F can be used to sterilize the first section 403 and gas or "dry" sterilization techniques can be used to sterilize components 430, 428, 470, 472, 410, 424 as well as the portion of the delivery device (e.g., a shaft (not shown) inserted within the aperture 424).

The first stage of assembly 400 of the embodiment of FIGS. 23-25D includes preparing the Tyvek® or similar material seals 470, 472. The seals 428, 470 are together placed into the second section 413. The lid 410 is then loosely attached to the second section 413 with the Tyvek® seal 470 placed between the respective threads of the lid 410 and the second section 413. Without the prosthetic valve or implant loaded thereto, the spindle 56 is inserted through the opening in the assembly (including elements 410 470, 428, 472 and 413) and moved distally away from the spindle 56. This is to allow for the attachment of the prosthetic valve 10 to the spindle 56.

Next, the prosthetic valve 10 is attached to the spindle 56. The Tyvek® or similar material seal 430 is prepared and placed on the second section 413 such that the exposed threads are covered. The first section 403 is filled with a sterilizing fluid F (e.g., glutaraldehyde or the like). The sterilizing fluid can be effective for both sterilizing the contents of the first section 403 and also preventing the prosthetic valve 10 from drying out. This assembly (including elements 410, 470, 428, 472, 413 and 430) is slid proximally towards a distal tip of the spindle 56.

To assemble and seal the assembly 400, the prosthetic valve 10 is put into the sterilizing solution and the second section 413 is screwed onto the assembly, sealing the second section 413 such that assembly 400 lies between the threads of the first section 403 and the second section 413. The lid cap 410 is then tightened compressing the seal 428 such that the first section 403 is sealed preventing the sterilizing solution from escaping the first section 403.

To begin the sterilization process, the assembly 400 is sealed within a gas permeable sealed tray or gas permeable pouch (not shown) and then sterilized with ethylene oxide (EtO) gas or the like. The Tyvek® or similar material seals (430, 470, 472) allow the ingress of the sterilant into the threaded areas of the assembly 400 while preventing the escape of the sterilizing fluid F contained within the first section 403. The use of the Tyvek® seals allows for this sterilization process to sterilize areas which otherwise would not be sterilized either by the "dry" sterilization techniques (e.g., EtO gas) or glutaraldehyde. Unsterile sections of the spindle 56 or the container 402 would make the spindle 56 unusable as the risk of non-sterile contamination to the end user is expected.

Tyvek® has outstanding moisture resistance and is a particularly beneficial material for seals 430, 470, 472. When water or other water-based fluids are in contact with Tyvek® such fluids do not wet the surface or spread; the water simply remains as droplets on the surface. Tyvek® is hydrophobic and does not absorb moisture. In addition to its moisture resistance, another advantage of Tyvek® is that a high moisture vapor transmission rate (MVTR) can be achieved. This is particularly important for an EtO sterilization process where water is introduced as a vapor because moisture enhances the effectiveness of EtO as a sterilant.

Although the present disclosure has been described with reference to preferred embodiments, workers skilled in the art will recognize that changes can be made in form and detail without departing from the spirit and scope of the present disclosure.

What is claimed is:

1. An assembly including:
an elongated delivery device;
an implant loaded onto a first portion of the elongated delivery device;
a storage container including a first section and a second section; wherein the implant is positioned within the first section and the first portion of the delivery device is positioned in both the first and second sections;
a first seal positioned to retain sterilization fluid within the first section; and
a second seal positioned between at least a portion of the delivery device and the second section, wherein the first seal is impermeable to liquid and the second seal is gas permeable.

2. The assembly of claim 1, wherein the first section is filled with sterilization fluid.

3. An assembly including:
an elongated delivery device comprising a first portion;
an implant loaded onto the first portion;
a storage container including a first section and an inlet tube comprising an open end; wherein the implant is positioned within the first section and the first portion of the elongated delivery device is positioned in the first section, through the inlet tube, and through the open end;
sterilization fluid at least partially filling the first section; and
a first seal impermeable to liquid positioned to retain sterilization fluid within the first section, wherein the first seal is placed to seal a space between the first portion of the elongated delivery device and an interior of the inlet tube at an intermediate location of the inlet tube, and an outer segment of the interior of the inlet tube between the open end and the first seal is dry and free from sterilization fluid.

4. The assembly of claim 3, wherein the first portion of the elongated delivery device comprises a spindle.

5. The assembly of claim 3, wherein the first section of the storage container comprises a storage area comprising a closed end opposite the open end of the inlet tube.

6. The assembly of claim 3, wherein the first seal comprises a mechanical seal.

7. The assembly of claim 3, wherein the storage container comprises a non-porous material.

8. The assembly of claim 7, wherein the non-porous material comprises film.

9. The assembly of claim 7, wherein the non-porous material comprises glass.

10. The assembly of claim 3, wherein the sterilization fluid comprises glutaraldehyde.

\* \* \* \* \*